United States Patent

Rossini et al.

[11] Patent Number: 5,945,640
[45] Date of Patent: Aug. 31, 1999

[54] STETHOSCOPE CHESTPIECE HAVING TWO SUSPENDED DIAPHRAGMS

[75] Inventors: Mary Jo Rossini; Thomas J. Packard, both of St. Paul, Minn.

[73] Assignee: 3M Innovative Properties Company, St. Paul, Minn.

[21] Appl. No.: 08/904,384

[22] Filed: Aug. 1, 1997

[51] Int. Cl.⁶ ..................................................... A61B 7/02
[52] U.S. Cl. ........................................... 181/131; 181/137
[58] Field of Search ................................... 181/131, 137; 381/67; 600/528

[56] References Cited

U.S. PATENT DOCUMENTS

| | | |
|---|---|---|
| 965,174 | 7/1910 | Fuchs ........................................ 181/131 |
| 3,108,652 | 10/1963 | Littmann . |
| 3,124,211 | 3/1964 | Cefaly ...................................... 181/131 |
| 3,152,659 | 10/1964 | Littmann . |
| 3,168,160 | 2/1965 | Littmann et al. . |
| 3,168,161 | 2/1965 | Littmann . |
| 3,215,224 | 11/1965 | Machlup . |
| 3,224,526 | 12/1965 | Weber . |
| 3,276,563 | 10/1966 | Fitzgerald et al. . |
| 3,303,903 | 2/1967 | Speelman et al. . |
| 3,366,198 | 1/1968 | Littmann . |
| 3,504,760 | 4/1970 | Littmann . |
| 3,515,239 | 6/1970 | Machlup et al. . |
| 4,200,167 | 4/1980 | Cockman et al. . |
| 4,200,169 | 4/1980 | MacDonald, III et al. . |
| 4,200,269 | 4/1980 | Ludwig . |
| 4,440,258 | 4/1984 | Packard . |
| 4,475,619 | 10/1984 | Packard . |
| 4,770,270 | 9/1988 | Grimm . |
| 4,852,684 | 8/1989 | Packard . |
| 4,913,259 | 4/1990 | Packard . |
| 5,111,904 | 5/1992 | Packard et al. . |
| 5,324,471 | 6/1994 | Packard et al. . |
| 5,380,182 | 1/1995 | Packard et al. . |
| 5,449,865 | 9/1995 | Desnick et al. . |
| 5,616,890 | 4/1997 | Bossignac ............................... 181/131 |

Primary Examiner—Khanh Dang
Attorney, Agent, or Firm—Gary L. Griswold; Eloise J. Maki; Jeffrey J. Hohenshell

[57] ABSTRACT

A stethoscope has a dual-sided stethoscope head. The stethoscope head includes a body member having first and second opposite sound collecting sides. Each of the first and second sound collecting sides has a suspended diaphragm member. Preferably, one side is specially adapted for use with adult patients while the other side is specially adapted for use with pediatric or thin patients where it is difficult to obtain good surface contact.

12 Claims, 5 Drawing Sheets

STETHOSCOPE CHESTPIECE HAVING TWO SUSPENDED DIAPHRAGMS

FIELD OF THE INVENTION

The present invention relates to stethoscopes. More particularly, it relates to dual sided stethoscope chestpieces which can be adjusted or tuned to vary the frequency response of the stethoscope head.

BACKGROUND OF THE INVENTION

The stethoscope is an important device utilized in a wide variety of medical fields. Particular examples of commercial stethoscopes include the 3M™ Littmann™ Master Cardiology and the 3M Littmann™ Cardiology II S.E. stethoscopes sold by Minnesota Mining and Manufacturing Co. (3M) of St. Paul, Minn. Examples of stethoscopes and stethoscope components are disclosed in U.S. Pat. Nos. 3,108,652; 3,152,659; 3,168,160; 3,168,161; 3,276,536; 3,366,198; 3,504,760; 4,200,269; 4,440,258; 4,475,619 and 5,111,904.

Complete diagnosis of a patient often requires that a physician monitor both low frequency and high frequency sounds associated with, for example, the heart. To conduct a diagnosis, stethoscope head constructions are known which comprise diametrically opposed diaphragm and open bell sides. The open bell side is generally designed to detect low frequency sounds, while the diaphragm side is generally designed to detect high frequency sounds. Dual-sided or "dual head" stethoscopes of this type are described, for example, in U.S. Pat. Nos. 3,108,652 (Littmann), 3,152,659 (Littmann), 3,215,224 (Machlup), 3,224,526 (Weber), 3,276,536 (Littmann), 3,303,903 (Speelman), and 3,515,239 (Machlup et al.).

A significant advancement in the stethoscope art is disclosed in U.S. Pat. No. 4,440,258 (Packard). That patent discloses a single sided stethoscope head with a suspended diaphragm. Commercially, a suspended diaphragm has also been incorporated on only one side of the 3M Littmann™ Cardiology II S.E. stethoscope. That commercial stethoscope includes a first sound collecting side having a suspended diaphragm and a second sound collecting side having an open bell without any diaphragm. Without a suspended diaphragm on the second sound collecting side of the 3M™ Littmann™ Cardiology II stethoscope, a user cannot make use of the advantages provided by a suspended diaphragm when using the open bell side of that stethoscope.

SUMMARY OF THE INVENTION

The present invention comprises a dual-sided stethoscope head that includes two suspended diaphragms. The stethoscope head comprises a body member having first and second opposite sound collecting sides. The stethoscope affords tuning in of sound while using either the first or the second side of the stethoscope head. The first sound collecting side is preferably sized and shaped to collect sounds from adult patients. The second sound collecting side is preferably sized and shaped to afford good surface contact on pediatric or thin patients. The second sound collecting side is also preferably substantially smaller than the first sound collecting side to afford easier access to remote or difficult to reach locations.

The first sound collecting side has a first recess with an innermost central portion, an outer rim portion, and an acoustic channel communicating with the central portion. A first diaphragm is also located on the first sound collecting side. The first diaphragm has a peripheral edge portion and a predetermined surface contour overlying at least a portion of the first recess. The first diaphragm is moveably connected to the outer rim portion of the first recess.

A first suspension member is also located on the first sound collecting side between the outer rim portion of the first recess and the peripheral edge portion of the first diaphragm. The suspension member connects the peripheral edge portion of the first diaphragm to the outer rim portion of the first recess to provide a first acoustical stiffness for the first diaphragm. The first suspension member also affords movement of the first diaphragm in a direction substantially perpendicular to the plane of the first diaphragm between: 1) a normal outer position to which the first diaphragm is biased by the first suspension member, and 2) an inner position more closely adjacent the central portion of the first recess. This movement is accomplished without substantially changing the surface contour of or the lateral tension in the first diaphragm.

A first immobilizing means is situated on the first sound collecting side of the stethoscope head. The first immobilizing means is located within the first recess. Together with the central portion of the first recess, the first immobilizing means forms a shallow recess within the first recess. The immobilizing means is sized and shaped to be contacted by one of the first diaphragm or the first suspension member (preferably the first diaphragm). When the first diaphragm is in the inner position, the immobilizing means immobilizes the first diaphragm.

The first sound collecting side of the stethoscope head will pass low frequency sounds and attenuate high frequency sounds when the first diaphragm is in the outer position and between the outer and inner positions. When the first diaphragm is in the inner position, the acoustical stiffness of the diaphragm will be significantly higher than the first acoustical stiffness so that the first sound collecting side of the stethoscope head will pass high frequency sounds and attenuate or block low frequency sounds.

The second sound collecting side has a second recess with an innermost central portion, an outer rim portion, and an acoustic channel communicating with the central portion. The second sound collecting side also has a second diaphragm with a peripheral edge portion and a predetermined surface contour overlying at least a portion of the second recess. The second diaphragm is moveably associated with the outer rim portion of the second recess.

A second suspension member is located between the outer rim portion of the second recess and the peripheral edge portion of the second diaphragm. The second suspension member connects the peripheral edge portion of the second diaphragm to the outer rim portion of the second recess to provide a first acoustical stiffness for the second diaphragm. The second suspension member also affords movement of the second diaphragm in a direction generally perpendicular to the plane of the second diaphragm between: 1) a normal outer position to which the second diaphragm is biased by the second suspension member, and 2) an inner position more closely adjacent the central portion of the second recess. The movement is made without substantially changing the surface contour of or the lateral tension in the second diaphragm.

A second immobilizing means is situated on the second sound collecting side of the stethoscope head. The second immobilizing means is located within the second recess. Together with the central portion of the second recess, the second immobilizing means forms a shallow recess within the second recess. The second immobilizing means is sized and shaped to be contacted by one of the second diaphragm or the second suspension member (preferably the second diaphragm). When the second diaphragm is in the inner position, the second immobilizing means immobilizes the second diaphragm.

The second sound collecting side of the stethoscope head will pass low frequency sounds and attenuate high frequency sounds when the second diaphragm is in the outer position and between the outer and inner positions. When the second diaphragm is in the inner position, the acoustical stiffness of the second diaphragm will be significantly higher than its first acoustical stiffness so that the second sound collecting side of the stethoscope head will pass high frequency sounds and attenuate or block low frequency sounds.

Preferably the size and shape of the first sound collecting side is different than the size and shape of the second sound collecting side. Also preferably, the second sound collecting side has a outer channel situated generally opposite the second recess. The outer channel is adapted to receive one of the second suspension member or a non-chill ring. When a non-chill ring is attached, the stethoscope has an open bell side. This feature affords modification of the stethoscope to suit those users who prefer an open bell, while at the same time affording the user the opportunity to convert that side of the stethoscope to one having the advantages of a suspended diaphragm.

The present invention may also be described as a stethoscope incorporating the stethoscope head as described above. Additionally, the present invention may be described as a kit comprising first and second suspended diaphragms, a non-chill ring, a stethoscope having ear tubes, ear tips, and a dual-sided stethoscope head, the stethoscope head comprising first and second sound collecting sides, the first sound collecting side being situated substantially opposite the second sound collecting side; the first sound collecting side having the first suspended diaphragm attached thereto, and the second sound collecting side having a means for connecting one of the second suspended diaphragm or the non-chill ring. The present invention may also be described as a method of using a stethoscope comprising manually removing the second suspended diaphragm and replacing it with a non-chill ring.

BRIEF DESCRIPTION OF THE DRAWINGS

The present invention will be further described with reference to the accompanying drawing wherein like reference numeral refer to like parts in the several views, and wherein.

DETAILED DESCRIPTION

As used in the instant specification and claims, "acoustical stiffness" of a diaphragm designates the mechanical stiffness of the diaphragm as influenced by the mechanical stiffness of the diaphragm material itself, the thickness of the diaphragm, the shape of the diaphragm, the diameter of the diaphragm, and the manner in which the diaphragm is attached to the stethoscope head. The phrase "plane of the diaphragm" refers to the generally planar surface of the diaphragm.

As used in the instant specification and claims, the phrase "suspended diaphragm" designates a diaphragm having at least a suspension member as described below. The diaphragm and suspension member are operatively associated with an immobilization means as described below. For example, the suspended diaphragm may be constructed according to the teachings of U.S. Pat. No. 4,440,258 to Packard (the entire contents of which are herein incorporated by reference).

Figure 1:
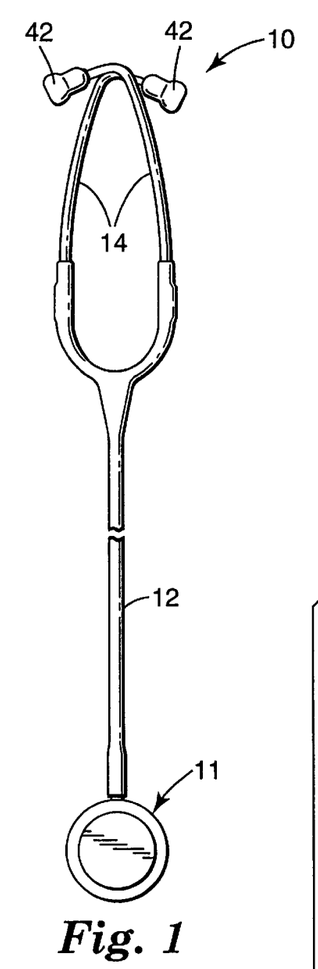
FIG. 1 is a schematic view of a stethoscope having a dual-sided stethoscope head in accordance with the present invention.

FIGS. 2–6 illustrate a preferred embodiment of a stethoscope head of the present invention. Referring first to FIG. 1, stethoscope head 10 comprises body member 11 formed of conventional material utilized in the fabrication of stethoscope heads, viz., metals such as stainless steel and aluminum, plastic, ceramics and wood. Stethoscope head 10 is attached to a conventional headset such as that described in U.S. Pat. No. 4,200,169 (herein incorporated by reference) which comprises elongated flexible tubing 12 which preferably contains dual air passages which run side-by-side for a major portion of the distance between stethoscope head 10 and ear tubes 14. The lower end of flexible tubing 12 is adapted to be coupled to a conventional stem fitting on the stethoscope head 10. The coupling may utilize the indexing detent as taught in U.S. Pat. No. 4,770,270 (the entire contents of which are herein expressly incorporated by reference). Binaural tubes for stethoscopes can be prepared in accordance with the teachings of U.S. Pat. Nos. 5,111,904; 5,380,182; and 5,324,471 to Packard et al. (each of which is hereby incorporated by reference).

Ear tips 42 are sized and shaped to engage the surfaces of the user's ears. The ear tips 42 may comprise any suitable ear tips. Preferably, the ear tips 42 comprise the soft ear tips disclosed in U.S. Pat. Nos. 4,852,684; 4,913,259 and 5,449,865 (the entire contents hereby incorporated by reference).

Ear tubes 14 could optionally be secured together by tubing which encloses a conventional prestressed leaf spring (not illustrated) as described in U.S. Pat. No. 4,200,167 (herein incorporated by reference in its entirety).

Figure 2:
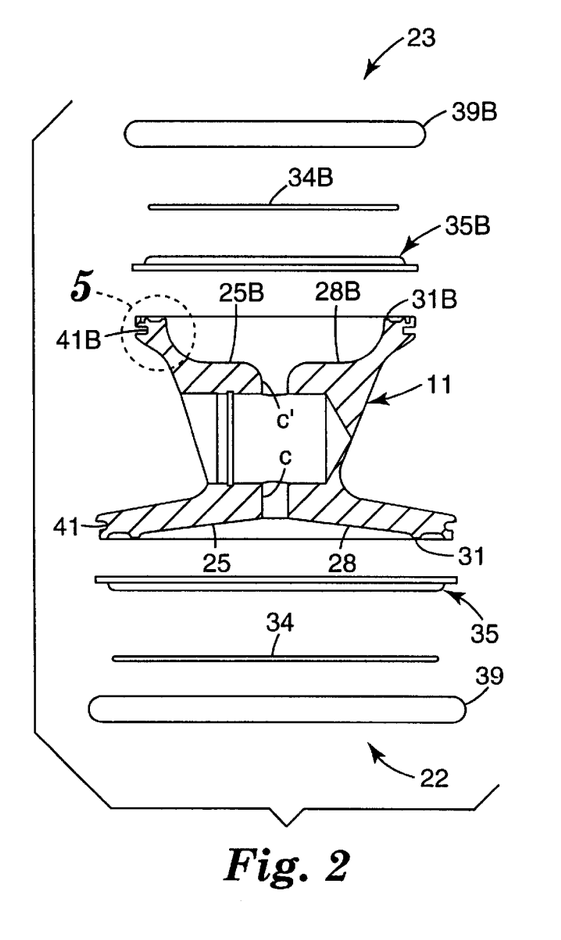
FIG. 2 is an enlarged, exploded, partial sectional view of the embodiment of the stethoscope head of FIG. 1.
Figure 3:
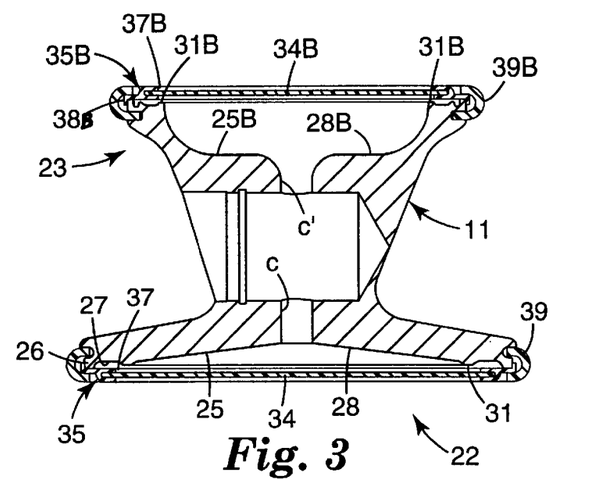
FIG. 3 is a cross sectional view of an assembled stethoscope head of the type shown in FIG. 2 showing first and second diaphragms in outer positions.
Figure 4:
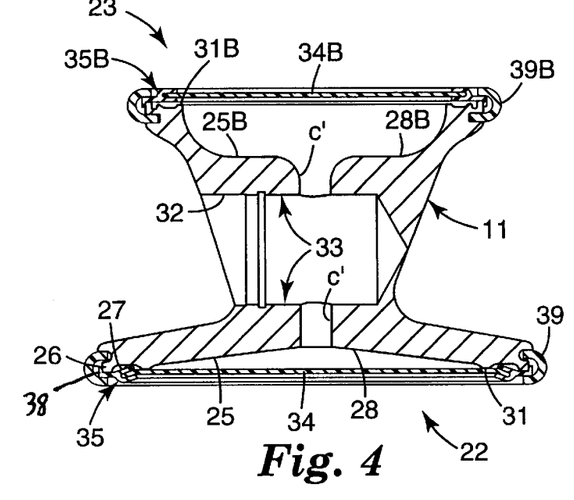
FIG. 4 is a cross sectional view of an assembled stethoscope head of the type shown in FIG. 2 showing a first diaphragm in an inner position and a second diaphragm in the outer position.
Figure 5:
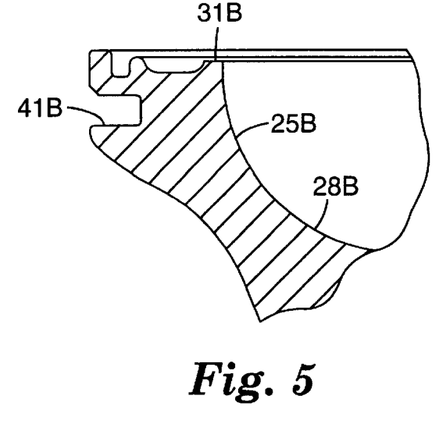
FIG. 5 is an enlarged detail view of a portion of the body of the stethoscope head of FIG. 2, taken approximately at the detail line 5 of FIG. 2.
Figure 6:
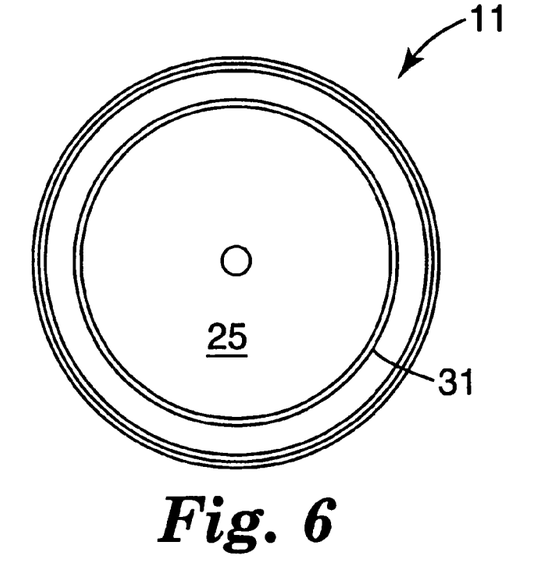
FIG. 6 is a side view of the first side of the body of the stethoscope head of FIG. 2.
Figure 7:
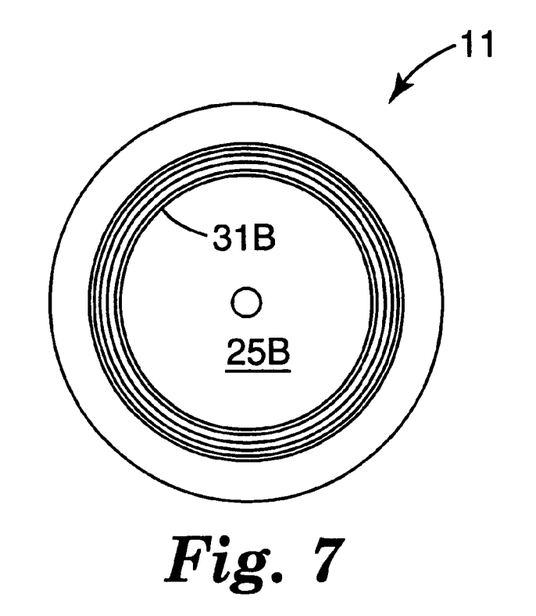
FIG. 7 is a side view of the second side of the body of the stethoscope head of FIG. 2.
Figure 8:
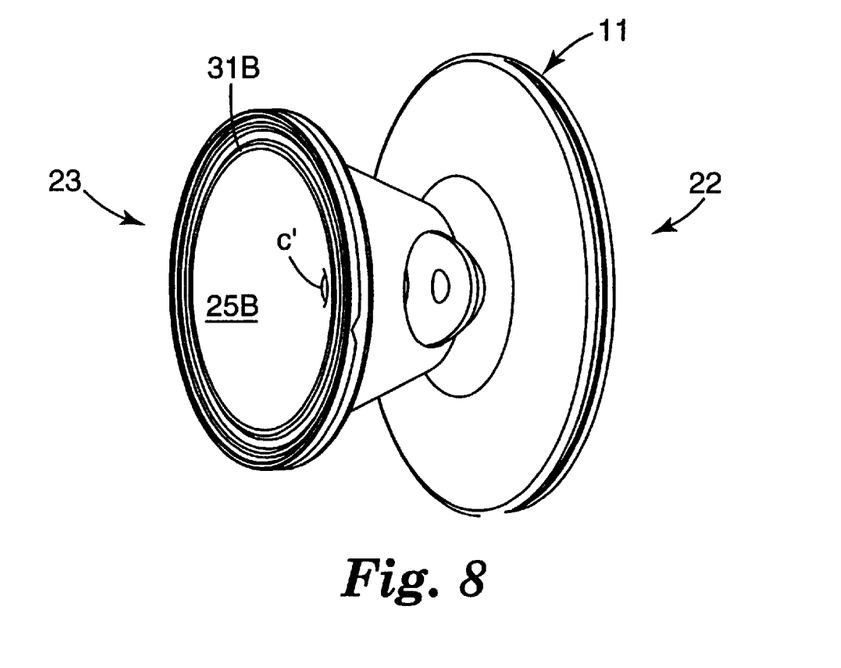
FIG. 8 is a perspective view of the body of the stethoscope head of FIG. 2.
Figure 9:
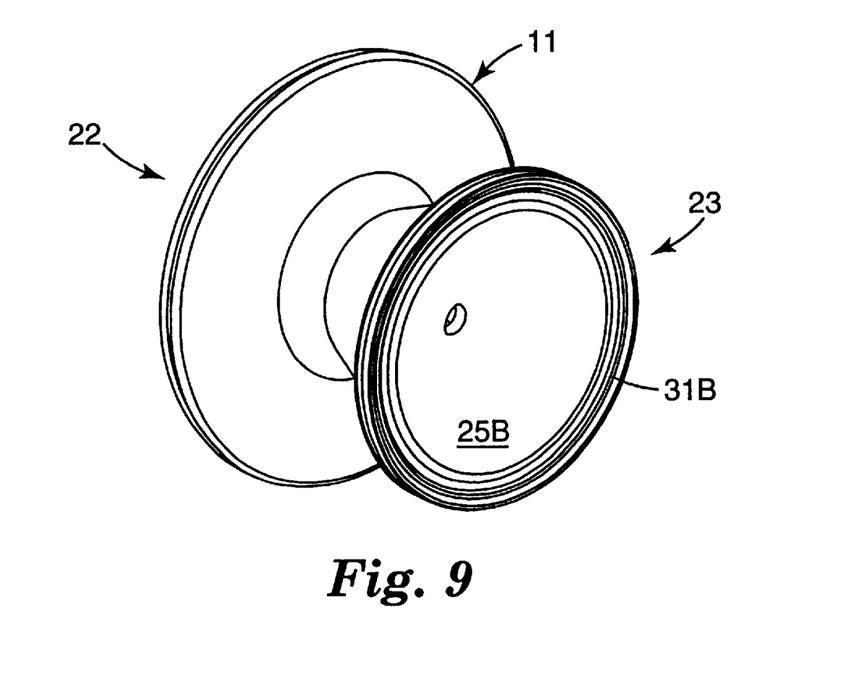
FIG. 9 is a perspective view of the body of the stethoscope head of FIG. 2 taken from a different perspective than the perspective view of FIG. 8.

Referring to FIGS. 2–4, the stethoscope head 11 is a dual-sided stethoscope head comprising a first sound collecting side 22 and a second sound collecting side 23. Preferably, the stethoscope 10 affords tuning in of sound while using either the first 22 or the second side 23 of the stethoscope head 11. The first sound collecting side 22 is preferably sized and shaped to collect sounds from adult patients. The second sound collecting side 23 is preferably sized and shaped to afford sufficient surface contact on pediatric or thin patients. The second sound collecting side 23 is also preferably substantially smaller than the first sound collecting side 22 to afford easier access to remote or difficult to reach locations.

The first sound collecting side 22 has a first recess 25 with an innermost central portion 28, an outer rim portion 27, and an acoustic channel 32, 33, C communicating with the central portion 28. A first diaphragm 34 is also located on the first sound collecting side 22. The first diaphragm 34 has a peripheral edge portion and a predetermined surface contour overlying at least a portion of the first recess 25. As shown in FIGS. 3 and 4, he first diaphragm 34 is moveably connected to or "operatively associated" with the outer rim portion 27 of the first recess 25.

A first suspension member 35 is also located on the first sound collecting side 22 between the outer rim portion 27 of the first recess 25 and the peripheral edge portion of the first diaphragm 34. The suspension member 35 connects the peripheral edge portion of the first diaphragm 34 to the outer rim portion 27 of the first recess 25 to provide a first acoustical stiffness for the first diaphragm 34. The first suspension member 35 also affords movement of the first diaphragm 34 in a direction substantially perpendicular to the plane of the first diaphragm 34 between: 1) a normal outer position (see FIG. 3) to which the first diaphragm 34 is biased by the first suspension member 35, and 2) an inner position (FIG. 4) more closely adjacent the central portion of the first recess 25. This movement is accomplished without substantially changing the surface contour of or the lateral tension in the first diaphragm 34 during the movement.

A first immobilizing means 31 is situated on the first sound collecting side 22 of the stethoscope head 11. The first immobilizing means 31 is located within the first recess 25. Together with the central portion of the first recess 25, the first immobilizing means 31 forms a shallow recess within the first recess 25. The immobilizing means 31 is sized and shaped to be contacted by at least one of the first diaphragm 34 or the first suspension member 35. In FIG. 4, it is the first diaphragm 34 which contacts the immobilizing means 31. When the first diaphragm 34 is in the inner position, the immobilizing means 31 immobilizes the first diaphragm 34.

The first sound collecting side 22 of the stethoscope head 11 will pass low frequency sounds and attenuate high frequency sounds when the first diaphragm 34 is in the outer position and between the outer and inner positions. When the first diaphragm 34 is in the inner position, the acoustical stiffness of the first diaphragm 34 will be significantly higher than the first acoustical stiffness so that the first sound collecting side 22 of the stethoscope head 11 will pass high frequency sounds and attenuate or block low frequency sounds. In use, a physician would simply modify the manual pressure exerted on the stethoscope head in order to switch between the outer and inner positions.

As described above in this Detailed Description portion of the present invention, the first sound collecting side 22 of the present invention is substantially identical to a first sound collecting side of the prior art 3M™ Littmann™ Cardiology II S.E. stethoscopes. Unlike the second sound collecting side of the 3M™ Littmann™ Cardiology II S.E. stethoscopes however, the second sound collecting side 23 is adapted to include a second suspended diaphragm.

The second sound collecting side 23 has many reference characters similar to the reference characters used to describe elements of the first sound collecting side 22 except that the reference character "B" has been added. The second sound collecting side 23 has a second recess 25B with an innermost central portion 28B, an outer rim portion 27B, and an acoustic channel C' communicating with the central portion 28B. Unlike the 3M™ Littmann™ Cardiology II stethoscopes, the second sound collecting side 23 has a second diaphragm 34B with a peripheral edge portion and a predetermined surface contour overlying at least a portion of the second recess 25B. The second diaphragm 34B is moveably associated with the outer rim portion 27B of the second recess 25B.

A second suspension member 35B is located between the outer rim portion 27B of the second recess 25B and the peripheral edge portion of the second diaphragm 34B. The second suspension member 35B connects the peripheral edge portion of the second diaphragm 34B to the outer rim portion 27B of the second recess 25B to provide a first acoustical stiffness for the second diaphragm 34B. The second suspension member 35B also affords movement of the second diaphragm 34B in a direction generally perpendicular to the plane of the second diaphragm 34B between: 1) a normal outer position to which the second diaphragm 34B is biased by the second suspension member 35B, and 2) an inner position more closely adjacent the central portion 28B of the second recess 25B. The movement is made without substantially changing the surface contour of or the lateral tension in the second diaphragm 34B.

A second immobilizing means 31B is situated on the second sound collecting side 23 of the stethoscope head 11. The second immobilizing means 31B is located within the second recess 25B. Together with the central portion 28B of the second recess 25B, the second immobilizing means 31B forms a shallow recess within the second recess 25B. The second immobilizing means 31B is sized and shaped to be contacted by one of the second diaphragm 34B or the second suspension member 35B (preferably the second diaphragm 34B). When the second diaphragm 34B is in the inner position, the second immobilizing means 31B immobilizes the second diaphragm 34B.

The second sound collecting side 23 of the stethoscope head 11 will pass low frequency sounds and attenuate high frequency sounds when the second diaphragm 34B is in the outer position and between the outer and inner positions. When the second diaphragm 34B is in the inner position, the acoustical stiffness of the second diaphragm 34B will be significantly higher than its first acoustical stiffness so that the second sound collecting side 23 of the stethoscope head 11 will pass high frequency sounds and attenuate or block low frequency sounds.

Preferably the size and shape of the first sound collecting side 22 is different than the size and shape of the second sound collecting side 23. Also preferably, the second sound collecting side 23 has a outer channel 41B situated generally opposite the second recess 25B. The outer channel 41B is adapted to receive one of the second suspension member 35B or a non-chill ring.

Figure 10:
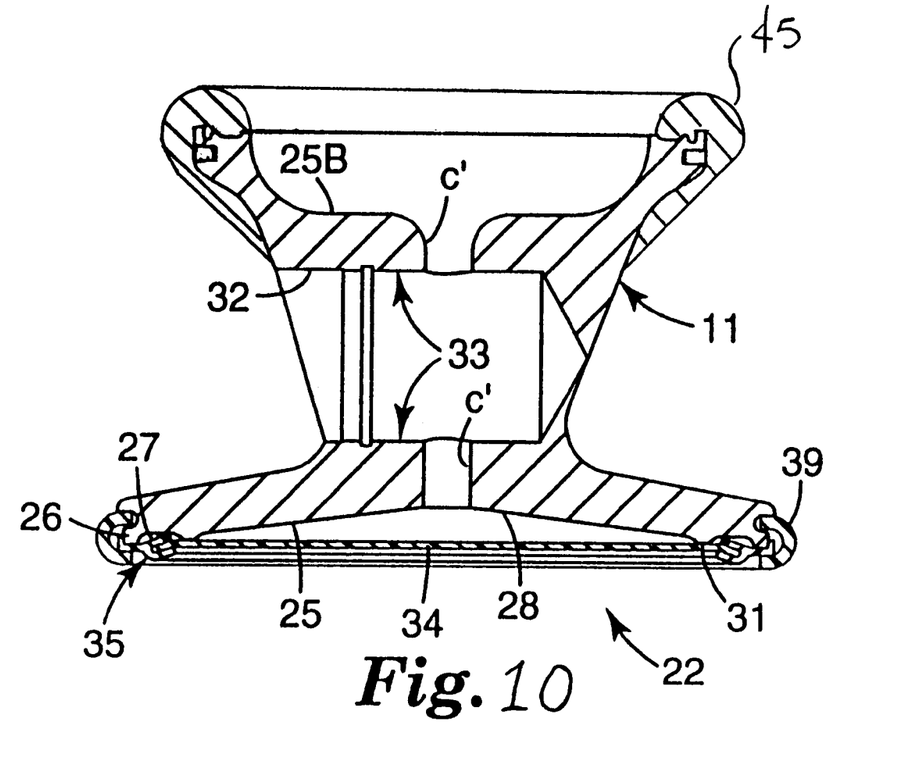
FIG. 10 is a sectional view illustrating an optional non-chill ring which may be alternatively attached to the second side of the stethoscope head.

As seen in FIG. 10, a non-chill ring 45 can be attached to the stethoscope 10 to provide an open bell side. This feature affords modification of the stethoscope 10 to suit those users who prefer an open bell, while at the same time affording the user the opportunity to convert that side of the stethoscope 10 to one having the advantages of a suspended diaphragm. Preferably, the non-chill ring 45 is sized to cover ridge 31B. It is particularly convenient to provide the invention as a kit including a stethoscope as has been described, two suspended diaphragms, and a non-chill ring adapted to attach to one of the sound collecting sides of the chestpiece of the stethoscope.

Preferably, the immobilizing means 31 and 31B comprise ridges machined into the metal of the stethoscope head 11 (see FIGS. 3 and 4). Other immobilizing means which are suitable for employment in the stethoscope heads of the present invention include O-rings, molded ridges, and inserts (e.g., plastic inserts). For example, the machined ridge 31B may have an inner diameter of about 1.053 inches, a depth radius of about 0.016 inches, and a width of 0.015 inches.

The diaphragms 34 and 34B overlay their respective recesses 25 and 25B sufficiently to afford contact of the diaphragms with the immobilizing means 31 and 31B. The diaphragms 34 and 34B may comprises any material which is known in the art as being suitable for use as a diaphragm. Examples of suitable materials include plastics such as polyester, fiberglass-reinforced plastics and polystyrene and metals such as stainless steel. A suitable thickness for diaphragm 34B is about 5 to 20 mils (0.013 to 0.051 centimeters). A preferred diaphragm 34B comprises a 0.01 mil-thick epoxy resin-fiberglas laminate, generally available from InsulFab, generally located in Franklin, N.H.

The suspension members or complaint rings 35 and 35B suspend their respective diaphragms 34 and 34B across their respective recesses 25 and 25B. Complaint rings 35 and 35 B are generally horseshoe-shaped in cross-section and have inner edges 37 and 37B and outer edges 38 and 38B. The complaint rings 35 and 35B are attached to peripheral edge portions of their respective diaphragms 34 and 34B at inner edges 37 and 37B. The outer edges 38 and 38B are preferably attached to their respective recesses 25 and 25B by means of a retaining ring or plastic fitting 39 and 38B which engages notches (e.g. 41B) of body member 11.

Complaint rings 35 and 35B comprise resilient materials and at least portions of them readily deform to provide facile movement of the diaphragms 34 and 34B. This construction of compliant rings 35 and 35B provides a first acoustical stiffness for the diaphragms 34 and 34B and permits movement of diaphragms 34 and 34B in a direction generally perpendicular to the plane of diaphragms 34 and 34B between a normal outer position to which diaphragms 34 and 34B are biased by compliant rings 35 and 35B and an inner position more closely adjacent central portions 28 and 28B. When the diaphragms 34 and 34B are in the inner positions, they are in contact with immobilizing means 31 and 31B and exhibit a significantly higher acoustical stiffness than the first acoustical stiffness. The surface contour of and the lateral tension in the diaphragms 34 and 34B does not change substantially during movement of diaphragms between the outer positions and the inner positions.

Examples of suitable materials for compliant rings 35 and 35B are elastomeric polyurethanes, silicone rubbers, thermoplastic rubbers, neoprenes and latexes. A suitable thickness for compliant ring 35B is 0.026 inches (maximum thickness). A preferred ring 35B comprises Bay silicone LSR 2540 rubber (e.g., generally available from Accusil, Inc. of Merrillville, Ind.). It is to be understood that the compliant ring 35 and diaphragm 34 may be formed as an integral member during fabrication. Likewise, the compliant ring 35B and diaphragm 34B may be formed as an integral member during fabrication.

It is also believed that a particular diaphragm and suspension member may be formed from a single sheet or film of material. In this regard it is to be understood that the term "diaphragm" as used in the instant application and claims designates that portion of the diaphragm-suspension member composite which substantially overlies the inner central portion of the body member and is capable of undergoing the desired planar movement without a substantial change in surface contour or lateral tension.

Compliant ring 35 is generally air-impervious. As a result, it may be desirable to provide a diaphragm with a hole therein in order to facilitate movement of the diaphragm. In the absence of such a hole, an air-tight system is created within stethoscope head 10 when the stethoscope is in use. Such an air-tight system may result in a formation of a vacuum which can inhibit facile movement of diaphragm from its position adjacent second conical-shaped recess.

The response of stethoscope head 10 to low frequency and high frequency sounds is affected by several parameters. The thickness of diaphragms affect the response and suitable thicknesses for the diaphragms have been discussed hereinabove. Also, the relative dimensions of first bell-shaped recess and second conical-shaped recess affect the response. The following have been found to be suitable dimensions for the recess 25B: The recess 25B has a diameter of about 1.32 inches, a major radius as seen in FIGS. 3 and 4 of about 0.196 inches, an initial major depth of about 0.22 inches and a secondary depth of about 0.235 inches. The passage C' has a diameter of about 0.125 inches.

It is contemplated that the acoustical stiffness of the diaphragm can be increased suitably by contact of the suspension member with the immobilizing means. For example, where the suspension member comprises a compliant ring similar to compliant ring 35 above, the desired increase in acoustical stiffness in the diaphragm can be achieved by contact of the suspension member and not the diaphragm with the immobilizing means. The portion of the suspension member which contacts the immobilizing means should be situated such that the diaphragm is substantially immobilized upon such contact.

It is to be understood that other variations and modifications can be made without departing from the spirit and scope of the invention.

We claim:

1. A dual-sided stethoscope head comprising:
  a body member having first and second opposite sound collecting sides,
  said first sound collecting side having a first recess with an innermost central portion, an outer rim portion, and an acoustic channel communicating with said central portion of said first recess;
  a first diaphragm having a peripheral edge portion and a predetermined surface contour overlying at least a portion of said first recess and moveably associated with the outer rim portion of said first recess;
  a first suspension member located between said outer rim portion of said first recess and the peripheral edge portion of said first diaphragm for associating said peripheral edge portion of said first diaphragm with said outer rim portion of said first recess to provide a first acoustical stiffness for said first diaphragm, and for affording movement of said first diaphragm in a direction generally perpendicular to the plane of said first diaphragm between a normal outer position to which said first diaphragm is biased by said first suspension member and an inner position more closely adjacent said central portion of said first recess without substantially changing the surface contour of or the lateral tension in said first diaphragm during said movement;

a first immobilizing means situated on said first sound collecting side of the stethoscope head and located within said first recess, and together with said central portion forming a shallow recess within said first recess, said immobilizing means adapted to be contacted by at least one of said first diaphragm or said first suspension member and to immobilize said first diaphragm when said first diaphragm is in said inner position so that 1) said first sound collecting side of said stethoscope head will pass low frequency sounds and attenuate high frequency sounds when said first diaphragm is in said outer position and between said outer and inner positions, and 2) when said first diaphragm is in said inner position the acoustical stiffness of said diaphragm will be significantly higher than said first acoustical stiffness so that said first sound collecting side of the stethoscope head will pass high frequency sounds and attenuate low frequency sounds;

said second sound collecting side having a second recess with an innermost central portion, an outer rim portion, and an acoustic channel communicating with said central portion of said second recess;

a second diaphragm having a peripheral edge portion and a predetermined surface contour overlying at least a portion of said second recess and moveably associated with the outer rim portion of said second recess;

a second suspension member located between said outer rim portion of said second recess and the peripheral edge portion of said second diaphragm for associating said peripheral edge portion of said second diaphragm with said outer rim portion of said second recess to provide a first acoustical stiffness for said second diaphragm, and for affording movement of said second diaphragm in a direction generally perpendicular to the plane of said second diaphragm between a normal outer position to which said second diaphragm is biased by said second suspension member and an inner position more closely adjacent said central portion of said second recess without substantially changing the surface contour of or the lateral tension in said second diaphragm during said movement; and second immobilizing means situated on said second sound collecting side of the stethoscope head and located within said second recess, and together with said central portion forming a shallow recess within said second recess, said second immobilizing means adapted to be contacted by at least one of said second diaphragm or said second suspension member and to immobilize said second diaphragm when said second diaphragm is in said inner position so that 1) said stethoscope head will pass low frequency sounds and attenuate high frequency sounds when said second diaphragm is in said outer position and between said outer and inner positions, and 2) when said second diaphragm is in said inner position the acoustical stiffness of said second diaphragm will be significantly higher than its first acoustical stiffness so that said second sound collecting side of the stethoscope head will pass high frequency sounds and attenuate low frequency sounds.

2. A dual-sided stethoscope head according to claim 1 wherein said first and second sound collecting sides each have a size and shape; and said size and shape of said first sound collecting side is different than said size and shape of said second sound collecting side.

3. A dual-sided stethoscope head according to claim 2 wherein said first sound collecting side is adapted to collect sounds from adult patients; and said second sound collecting side is adapted to afford surface contact on pediatric or thin patients.

4. A dual sided stethoscope head according to claim 1 wherein said second sound collecting side has a outer channel situated generally opposite said second recess, said outer channel being adapted to receive one of said second suspension member or a non-chill ring.

5. A dual sided stethoscope head according to claim 1 wherein said first immobilizing means comprises a metal ridge machined into the first sound collecting side of the stethoscope head, and said second immobilizing means comprises a metal ridge machined into the second sound collecting side of the stethoscope head.

6. A stethoscope adapted to deliver sound to a human user, the stethoscope comprising:

a pair of ear tips;

a pair of tubes in acoustic communication with the eartips; and a dual-sided stethoscope head in acoustic communication with the tubes;

said dual-sided stethoscope head comprising:

a body member having first and second opposite sound collecting sides, said first sound collecting side having a first recess with an innermost central portion, an outer rim portion, and an acoustic channel communicating with said central portion of said first recess;

a first diaphragm having a peripheral edge portion and a predetermined surface contour overlying at least a portion of said first recess and moveably associated with the outer rim portion of said first recess;

a first suspension member located between said outer rim portion of said first recess and the peripheral edge portion of said first diaphragm for associating said peripheral edge portion of said first diaphragm with said outer rim portion of said first recess to provide a first acoustical stiffness for said first diaphragm, and for affording movement of said first diaphragm in a direction generally perpendicular to the plane of said first diaphragm between a normal outer position to which said first diaphragm is biased by said first suspension member and an inner position more closely adjacent said central portion of said first recess without substantially changing the surface contour of or the lateral tension in said first diaphragm during said movement;

a first immobilizing means situated on said first sound collecting side of the stethoscope head and located within said first recess, and together with said central portion forming a shallow recess within said first recess, said immobilizing means adapted to be contacted by at least one of said first diaphragm or said first suspension member and to immobilize said first diaphragm when said first diaphragm is in said inner position so that 1) said first sound collecting side of said stethoscope head will pass low frequency sounds and attenuate high frequency sounds when said first diaphragm is in said outer position and between said outer and inner positions, and 2) when said first diaphragm is in said inner position the acoustical stiffness of said diaphragm will be significantly higher than said first acoustical stiffness so that said first sound collecting side of the stethoscope head will pass high frequency sounds and attenuate low frequency sounds;

said second sound collecting side having a second recess with an innermost central portion, an outer rim portion, and an acoustic channel communicating with said central portion of said second recess;

a second diaphragm having a peripheral edge portion and a predetermined surface contour overlying at least a portion of said second recess and moveably associated with the outer rim portion of said second recess;

a second suspension member located between said outer rim portion of said second recess and the peripheral edge portion of said second diaphragm for associating said peripheral edge portion of said second diaphragm with said outer rim portion of said second recess to provide a first acoustical stiffness for said second diaphragm, and for affording movement of said second diaphragm in a direction generally perpendicular to the plane of said second diaphragm between a normal outer position to which said second diaphragm is biased by said second suspension member and an inner position more closely adjacent said central portion of said second recess without substantially changing the surface contour of or the lateral tension in said second diaphragm during said movement; and second immobilizing means situated on said second sound collecting side of the stethoscope head and located within said second recess, and together with said central portion forming a shallow recess within said second recess, said second immobilizing means adapted to be contacted by at least one of said second diaphragm or said second suspension member and to immobilize said second diaphragm when said second diaphragm is in said inner position so that 1) said stethoscope head will pass low frequency sounds and attenuate high frequency sounds when said second diaphragm is in said outer position and between said outer and inner positions, and 2) when said second diaphragm is in said inner position the acoustical stiffness of said second diaphragm will be significantly higher than its first acoustical stiffness so that said second sound collecting side of the stethoscope head will pass high frequency sounds and attenuate low frequency sounds.

7. A stethoscope according to claim 6 wherein said first and second sound collecting sides each have a size and shape; and said size and shape of said first sound collecting side is different than said size and shape of said second sound collecting side.

8. A stethoscope according to claim 7 wherein said first sound collecting side is adapted to collect sounds from adult patients; and said second sound collecting side is adapted to afford surface contact on pediatric or thin patients.

9. A stethoscope according to claim 6 wherein said second sound collecting side has a outer channel situated generally opposite said second recess, said outer channel being adapted to receive one of said second suspension member or a non-chill ring.

10. A stethoscope according to claim 6 wherein said first immobilizing means comprises a metal ridge machined into the first sound collecting side of the stethoscope head, and said second immobilizing means comprises a metal ridge machined into the second sound collecting side of the stethoscope head.

11. In combination, a stethoscope assembly comprising:

first and second suspended diaphragm assemblies, a non-chill ring, a stethoscope having ear tubes, ear tips, and a dual-sided stethoscope head, the stethoscope head comprising first and second sound collecting sides, said first sound collecting side being situated substantially opposite said second sound collecting side;

said first sound collecting side having the first suspended diaphragm assembly attached thereto, and said second sound collecting side having structure that is sized and shaped to accept either the second suspended diaphragm assembly or the non-chill ring.

12. A method of using a stethoscope assembly comprising the steps of:

(1) providing a stethoscope assembly having ear tubes, ear tips, and a dual-sided stethoscope head, the stethoscope head comprising first and second sound collecting sides, said first sound collecting side being situated substantially opposite said second sound collecting side;

said first sound collecting side having a first suspended diaphragm attached thereto, the stethoscope assembly including a second suspended diaphragm and a non-chill ring, and said second sound collecting side having structure that is sized and shaped to accept either the second suspended diaphragm or the non-chill ring; and (2) manually attaching either the second suspended diaphragm or the non-chill ring to said second sound collecting side.

* * * * *